United States Patent [19]

Peet et al.

[11] Patent Number: 5,426,101

[45] Date of Patent: Jun. 20, 1995

[54] 2-SUBSTITUTED ADENOSINES WITH A-2 RECEPTOR AFFINITY

[75] Inventors: Norton P. Peet, Cincinnati; David R. Borcherding, Loveland; Nelsen L. Lentz, West Chester; Philip M. Weintraub, Cincinnati; Philip R. Kastner, Loveland, all of Ohio

[73] Assignee: Merrell Dow Pharmaceuticals Inc., Cincinnati, Ohio

[21] Appl. No.: 306,847

[22] Filed: Sep. 15, 1994

Related U.S. Application Data

[63] Continuation of Ser. No. 169,341, Dec. 17, 1993, abandoned, which is a continuation-in-part of Ser. No. 954,180, Sep. 30, 1992, abandoned.

[51] Int. Cl.$^6$ .................. C07H 19/167; A61K 31/70
[52] U.S. Cl. ..................................... 514/46; 536/27.61
[58] Field of Search ............... 536/27.61, 27.62, 27.63, 536/27.81; 514/46

[56] References Cited

U.S. PATENT DOCUMENTS

| | | | |
|---|---|---|---|
| 4,626,526 | 12/1986 | Bristol | 514/46 |
| 4,837,207 | 6/1989 | Trivedi et al. | 514/46 |
| 4,992,535 | 2/1991 | Libert et al. | 514/46 |
| 5,030,624 | 7/1991 | Lowrie et al. | 514/46 |
| 5,032,584 | 7/1991 | Lowrie et al. | 514/46 |
| 5,034,381 | 7/1991 | Hutchison et al. | 514/26 |

FOREIGN PATENT DOCUMENTS 323807  7/1989  European Pat. Off. .

OTHER PUBLICATIONS

Francis, J. E., "Highly Selective Adenosine A2 Receptor Agonists in a Series of N-Alkylated 2-Aminoadenosines", J. Med. Chem. 34:2570-2579, 1991.

Primary Examiner—Douglas W. Robinson
Assistant Examiner—Gary L. Kunz
Attorney, Agent, or Firm—Michael J. Sayles; Nelsen L. Lentz

[57] ABSTRACT

The compound (R)-2-[(phenylisopropyl)amino]adenosine whose structure is given below:

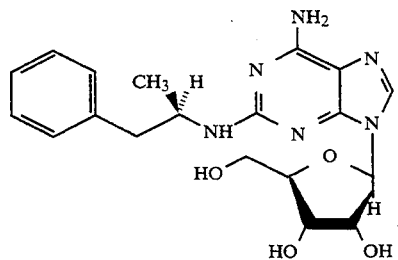

(R)-2-[(phenylisopropyl)amino]adenosine is about two orders of magnitude greater in its selectivity between the A-1 and A-2 adenosine receptors than its diastereoisomer. This compound is useful for lowering blood pressure.

4 Claims, No Drawings

2-SUBSTITUTED ADENOSINES WITH A-2 RECEPTOR AFFINITY

CROSS-REFERENCE TO RELATED APPLICATION

This is a continuation of application Ser. No. 08/169,341, filed Dec. 17, 1993 now abandoned, which is a continuation-in-part of application Ser. No. 07/954,180 filed Sep. 30, 1994, now abandoned which is herein incorporated by reference.

FIELD OF THE INVENTION

The present invention relates to a group of compounds which are adenosine analogues and which act selectively at adenosine receptors.

BACKGROUND OF THE INVENTION

The profound hypotensive, sedative, antispasmodic, and vasodilatory actions of adenosine were first recognized over 50 years ago. Subsequently, the number of biological roles proposed for adenosine have increased considerably. The adenosine receptors appear linked in many cells to adenylate cyclase. A variety of adenosine analogues have been introduced in recent years for the study of these receptor functions. Alkylxanthines, such as caffeine and theophylline, are the best known antagonists of adenosine receptors.

Adenosine perhaps represents a general regulatory substance, since no particular cell type or tissue appears uniquely responsible for its formation. In this regard, adenosine is unlike various endocrine hormones. Nor is there any evidence for storage and release of adenosine from nerve or other cells. Thus, adenosine is unlike various neurotransmitter substances.

Adenosine might be compared as a physiological regulator to the prostaglandins. In both cases the enzymes involved in the metabolic formation are ubiquitous and appear to be responsive to alterations in the physiological state of the cell. Receptors for adenosine, like those for prostaglandins, are proving to be very widespread. Finally, both prostaglandins and adenosine appear to be involved with the regulation of functions involving calcium ions. Prostaglandins, of course, derive from membrane precursors, while adenosine derives from cytosolic precursors.

Although adenosine can affect a variety of physiological functions, particular attention has been directed over the years toward actions which might lead to clinical applications. Preeminent have been the cardiovascular effects of adenosine which lead to vasodilation and hypotension but which also lead to cardiac depression. The antilipolytic, antithrombotic and antispasmodic actions of adenosine have also received some attention. Adenosine stimulates steroidogenesis in adrenal cells, again probably via activation of adenylate cyclase. Adenosine has inhibitory effects on neurotransmission and on spontaneous activity of central neurons. Finally, the bronchoconstrictor action of adenosine and its antagonism by xanthines represents an important area of research.

It has now been recognized that there are not one but at least two classes of extracellular receptors involved in the action of adenosine. One of these has a high affinity for adenosine and, at least in some cells, couples to adenylate cyclase in an inhibitory manner. These have been termed by some as the A-1 receptors. The other class of receptors has a lower affinity for adenosine and in many cell types couples to adenylate cyclase in a stimulatory manner. These have been termed the A-2 receptors.

Characterization of the adenosine receptors has now been possible with a variety of structural analogues. Adenosine analogues resistant to metabolism or uptake mechanisms have become available. These are particularly valuable, since their apparent potencies will be less affected by metabolic removal from the effector system. The adenosine analogues exhibit differing rank orders of potencies at A-1 and A-2 adenosine receptors, providing a simple method of categorizing a physiological response with respect to the nature of the adenosine receptor. The blockade of adenosine receptors (antagonism) provides another method of categorizing a response with respect to the involvement of adenosine receptors. It should be noted that the development of potent antagonists specific to A-1 or A-2 adenosine receptors would represent a major breakthrough in this research field and in the preparation of adenosine receptor selective pharmacological agents having specific physiological effects in animals.

SUMMARY OF THE INVENTION

The present invention relates to compounds of Formula I:

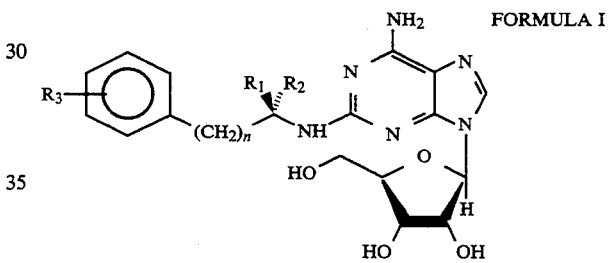

wherein $R_1$ and $R_2$ are each independently hydrogen or $C_1$-$C_4$ alkyl, $R_3$ is $C_1$-$C_4$ alkyl, $C_1$-$C_4$ alkoxy or halogen, and n is an integer from 0 to 3.

DETAILED DESCRIPTION OF THE INVENTION

As used herein the term "$C_1$-$C_4$ alkyl" refers to a saturated straight or branched chain hydrocarbon radical of one to four carbon atoms. Included within the scope of this term are methyl, ethyl, n-propyl, isopropyl, n-butyl, isobutyl and the like. The term "$C_1$-$C_4$ alkoxy" refers to an alkyloxy radical made up of an oxygen radical bearing a saturated straight or branched chain hydrocarbyl radical of one to four carbon atoms and specifically includes methoxy, ethoxy, propyloxy, isopropyloxy, n-butyloxy, iso-butyloxy, sec-butyloxy, tertiary butyloxy and the like. The term "halogen" refers to fluorine, chlorine, bromine, or iodine.

Stereoisomerism is possible with the present compounds and the chemical structure as presented above is considered as encompassing all of the possible stereoisomers and racemic mixtures of such stereoisomers. More specifically, when $R_1$ and $R_2$ are defined as in Formula I and are nonequivalent, the respective carbon atom is chiral and optical isomerism is possible.

As examples of compounds of the present invention are the following:

1. (R)-2-[(phenylisopropyl)amino]adenosine
2. (S)-2-[(phenylisopropyl)amino]adenosine 3. (R)-2-[(1-Phenylpropyl)amino]adenosine
4. (S)-2-[(1-Phenylpropyl)amino]adenosine The general synthetic process for compounds of Formula I is set forth in Scheme A. All the substituents, unless otherwise indicated, are previously defined. The reagents and starting materials for use in this process are readily available to one of ordinary skill in the art.

Scheme A

In Scheme A, step a, 2'- and 3'-hydroxyl groups of 2-chloroadenosine (1) are protected as the acetonide defined by structure (2). Following the general procedure of Hampton [i J. Am. Chem. Soc., 83, 3640 (1961)], an equivalent of 2-chloroadenosine is combined with approximately 10 equivalents of 2,2-dimethoxypropane and approximately 5 equivalents of p-toluenesulfonic acid in an appropriate

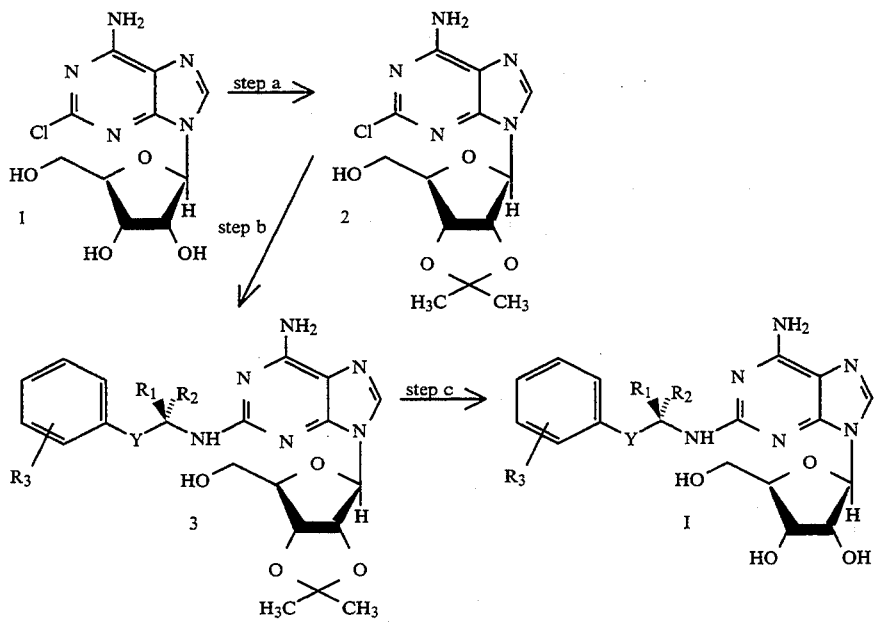

Y = $(CH_2)_n$ solvent such as N,N-dimethylformamide. After stirring at room temperature for approximately 20 hours the product is isolated and purified by techniques well-known to one skilled in the art. For example, an excess of a suitable aqueous base such as saturated sodium bicarbonate is added and the solvent is removed under vacuum. The residue is extracted with a suitable organic solvent such as chloroform, dried over magnesium sulfate, filtered and concentrated under vacuum. The crude product can be purified by flash chromatography or recrystallization methods to provide the acetonide (2).

In Scheme A, step b, the acetonide (2) is then treated with an appropriately substituted primary amine to provide the secondary amine of structure (3). More specifically, the acetonide (2) is combined with a large excess of an appropriately substituted primary amine, such as L-(−)-amphetamine, D-(+)-amphetamine, (R)-1-phenylpropylamine or (S)-1-phenylpropylamine, under an atmosphere of an inert gas such as nitrogen. The mixture is then heated to approximately 130° C. with stirring for approximately 3 to 6 hours. After cooling, the product can be isolated and purified by techniques well known to one skilled in the art. For example, the crude mixture can be directly purified by flash chromatography followed by radial chromatography using an appropriate eluent such as 3% to 6% methanol/chloroform to provide the secondary amine (3).

In Scheme A, step c, the secondary amine (3) is then deprotected under acidic conditions to provide the compound of Formula I. More specifically, the secondary amine (3) is treated with an excess of a suitable acid, such as 1M hydrochloric acid and heated to approximately 40° C. to 50° C. for about 30 minutes. After cooling, the product can be isolated and purified by techniques well-known to one skilled in the art. For example, the reaction is treated with an excess of a suitable weak base, such as saturated aqueous sodium bicarbonate and then extracted with a suitable organic solvent, such as chloroform. The organic extracts are dried over anhydrous magnesium sulfate, filtered and concentrated under vacuum. The crude residue can then be purified by chromatographic techniques, such as radial chromatography and then treated with ethereal hydrogen chloride to provide the hydrochloride salt of Formula I.

Therapeutic Utility Of Selective Adenosine Receptor Agents

The table below shows in more detail the potential therapeutic utility of selective adenosine receptor agents in accordance with the present invention:

| Area | Effect | Receptor Correlate |
| --- | --- | --- |
| Cardiovascular | cardiotonic | A-1 antagonism |
| Cardiovascular | control tachycardia | A-1 agonism |
| Cardiovascular | increase coronary blood flow | A-2 agonism |
| Cardiovascular | vasodilation | A-2 (atypical) agonism |
| Pulmonary | bronchodilation | A-1 antagonism |
| Pulmonary | mediation of autocoid release from mast cells, basophils | novel adenosine receptor interaction on cell surface |

| Area | Effect | Receptor Correlate |
|---|---|---|
| Pulmonary | stimulate respiration; treat paradoxical ventilatory response (infants) | Ado antagonism |
| Renal | inhibit renin release | A-1 agonism |
| Central Nervous System | aid in opiate withdrawal | Ado agonism |
| Central Nervous System | analgesic | A-1 agonism |
| Central Nervous System | anticonvulsant | A-1 agonism |
| Central Nervous System | antidepressant | A-1 agonism |
| Central Nervous System | antipsychotic | Ado agonism |
| Central Nervous System | anxiolytic | agonism |
| Central Nervous System | inhibition of self-mutilation behavior (Lesch-Nyhan syndrome) | Ado agonism |
| Central Nervous System | sedative | A-2 agonism |

In the cardiovascular, pulmonary and renal system targets, designed compounds which are identified by receptor binding studies can be evaluated in functional in vivo tests which are directly indicative of the human physiological response. A good description of the pharmacology and functional significance of purine receptors is presented by M. Williams in *Ann. Rev. Pharmacol. Toxicol.*, 27, 31 (1987). In a section entitled "Therapeutic Targeting of Adenosine Receptor Modulators" it is stated that "adenosine agonists may be effective as antihypertensive agents, in the treatment of opiate withdrawal, as modulators of immune competence and renin release, as antipsychotics and as hypnotics. Conversely, antagonists may be useful as central stimulants, inotropics, cardiotonics, antistress agents, antiasthmatics, and in the treatment of respiratory disorders." The smorgasbord of activities displayed by adenosine receptor agents underscores their great potential utility for therapy and the need for central agents.

Adenosine exerts its various biological effects via action on cell-surface receptors. These adenosine receptors are of two types, A-1 and A-2. The A-1 receptors are operationally defined as those receptors at which several 6C-N substituted adenosine analogs such as R-phenylisopropyladenosine (R-PIA) and cycloadenosine (CHA) are more potent than 2-chloroadenosine and N-5'-ethylcarboxamidoadenosine (NECA). At A-2 receptors the order of potency is instead NECA>2-chloroadenosine>R-PIA>CHA.

As illustrated in the table above, adenosine receptors govern a variety of physiological functions. The two major classes of adenosine receptors have already been defined. These are the A-1 adenosine receptor, which is inhibitory of adenylate cyclase, and the A-2 adenosine receptor, which is stimulatory to adenylate cyclase. The A-1 receptor has a higher affinity for adenosine and adenosine analogs than the A-2 receptor. The physiological effects of adenosine and adenosine analogs are complicated by the fact that nonselective adenosine receptor agents first bind the rather ubiquitous low-affinity A-2 receptors, then as the dose is increased, the high-affinity A-2 receptors are bound, and finally, at much higher doses, the very high-affinity A-1 adenosine receptors are bound. (See J. W. Daly, et al., *Subclasses of Adenosine Receptors in the Central Nervous System: Interaction with Caffeine and Related Methylxanthines*, *Cellular and Molecular Neurobiology*, 3,(1), 69–80 (1983).)

In general, the physiological effects of adenosine are mediated by either the stimulation or the inhibition of adenylate cyclase. Activation of adenylate cyclase increases the intracellular concentration of cyclic AMP, which, in general, is recognized as an intracellular second messenger. The effects of adenosine analogs can therefore be measured by either the ability to increase or the ability to antagonize the increase in the cyclic AMP in cultured cell lines. Two important cell lines in this regard are VA 13 (WI-38 VA 13 2RA), SV-40 transformed WI 38 human fetal lung fibroblasts, which are known to carry the A-2 subtype of adenosine receptor, and fat cells, which are known to carry the A-1 subtype of adenosine receptor. (See R. F. Bruns, *Adenosine Antagonism by Purines, Pteridines and Benzopteridines in Human Fibroblasts*, *Chemical Pharmacology*, 30, 325-33 (1981).)

It is well-known from in vitro studies that the carboxylic acid congener of 8-phenyl-1,3-dipropylxanthine (XCC) is adenosine receptor nonselective, with a $K_i$ at the A-1 receptor in rat brain membranes of 58±3 nM and a $K_i$ at the A-2 receptor of the rat brain slice assay of 34±13 nM. The amino congener of 8-phenyl-1,3-dipropylxanthine (XAC), on the other hand, has a 40-fold higher affinity for the A-1 adenosine receptor, with a $K_i$ of 1.2±0.5 nM, as compared with a $K_i$ at the A-2 receptor of 49±17 nM. In addition, XAC is much more potent in antagonizing the effects of adenosine analogs on heart rate than on blood pressure. Since it is generally known that the adenosine analog-induced effects on the heart seem to be mediated via A-1 receptors and those on blood pressure via A-2 receptors, the selectivity of XAC under in vivo conditions suggests that adenosine receptor activity in vitro correlates with adenosine receptor activity in vivo and that specific physiological effects can be distinguished as a result of this selectivity. (See B. B. Fredholm, K. A. Jacobsen, B. Jonzon, K. L. Kirk, Y. O. Li, and J. W. Daly, *Evidence That a Novel 8-Phenyl-Substituted Xanthine Derivative is a Cardioselective Adenosine Receptor Antagonist In Vivo*, *Journal of Cardiovascular Pharmacology*, 9, 396–400, (1987), and also K. A. Jacobsen, K. L. Kirk, J. W. Daly, B. Jonzon, Y. O. Li, and B. B. Fredholm, *Novel 8-Phenyl-Substituted Xanthine Derivative Is Selective Antagonist At Adenosine Receptors In Vivo*, *Acta Physiol. Scand.*, 341–42 (1985).)

It is also known that adenosine produces a marked decrease in blood pressure. This blood pressure reduction is probably dependent upon an A-2 receptor-mediated decrease in peripheral resistance. Adenosine analogs are also able to decrease heart rate. This effect is probably mediated via adenosine receptors of the A-1 subtype.

Cardiovascular Studies With
(R)-2-[(Phenylisopropyl)Amino]Adenosine in Anesthesized and Conscious Dogs Intravenous (R)-2-[(phenylisopropyl)amino]adenosine was tested in three anesthetized beagles for its effect on blood pressure and heart rate. All three beagles received a 1 mL bolus injection (in less than 15 sec.) of vehicle, 50% DMSO/50% 0.9% sodium chloride, prior to receiving (R)-2-[(phenylisopropyl)amino]adenosine. Two beagles received a single 0.1 mg/kg bolus injection of (R)-2-[(phenylisopropyl)amino]adenosine. (R)-2-

[(Phenylisopropyl)amino]adenosine decreased mean arterial pressure (MAP) 35 and 49 mmHg and increased heart rate (HR) 16 and 56 bpm. Peak response to (R)-2-[(phenylisopropyl)amino]adenosine occurred in less than 5 minutes. The MAP effect was sustained through the experiments but the HR effect waned. The third beagle recieved three 0.1 mg/kg doses of (R)-2-[(phenylisopropyl)amino]adenosine. Thirty minutes separated each dose. (R)-2-[(Phenylisopropyl)amino]adenosine lowered MAP 65 mmHG (115 mmHg to 50 mmHg) and increased HR 20 bpm (138 bpm to 158 bpm) after the first dose and the peak response occurred in less than 5 minutes. MAP remained at this level throughout the remainder of the study and subsequent doses had little additional effect on MAP or HR.

Intravenous (R)-2-[(phenylisopropyl)amino]adenosine was tested in two conscious beagles for its effect on blood pressure and heart rate. (R)-2-[(Phenylisopropyl)amino]adenosine was dissolved in 1 mL of 50% DMSO/50% 0.9% sodium chloride and was administered as a bolus injection (in less that 15 sec.). The compound (R)-2-[(phenylisopropyl)amino]adenosine decreased MAP in both dogs for 7 hours (maximum decrease as compared to vehicle was 37 mmHg three hours after dosing in one dog and 68 mmHg two hours after dosing in the second). HR was increased for up to 9 hours following (R)-2-[(phenylisopropyl)amino]adenosine. The maximum increase occurred 4 hours after dosing and was 60 bpm for both dogs.

In addition, one instrumented conscious beagle dog was administered a single 1.0 mg/kg dose of (R)-2-[(phenylisopropyl)amino]adenosine in a gelatin capsule. Blood pressure was decreased for up to 36 hours, exceeding 20 mmHG for the first 16 hours. Heart rate was increased 20-40 bpm for up to 12 hours.

Thus, it is readily apparent that the pharmacological administration of the adenosine receptor selective adenosine analogs disclosed herein will result in selective binding to either the A-2 or the A-1 receptor, which will, in turn, selectively result in either a decrease in blood pressure or a decrease in heart rate, for example, thereby decoupling these physiological effects in vivo. The selection of such adenosine receptor selective agents can be determined by the methods described in further detail below.

Test For Affinity For Brain Adenosine A-2 Receptors

The test described below was used to determine the potency of test compounds to compete with the ligand [3H]-5'-N-ethyl-carboxamidoadenosine (NECA) for the adenosine A-2 receptors prepared from animal brain membranes. (See also R. R. Bruns, G. H. Lu, and T. A. Pugsley, *Characterization of the A-2 Adenosine Receptor Labeled by [3H]NECA in Rat Striatal Membranes, Mol. Pharmacol.*, 29, 331-346 (1986).) Young male rats (C-D strain), obtained from Charles River, are killed by decapitation and the brains are removed. Membranes for ligand binding are isolated from rat brain striatum. The tissue is homogenized in 20 vol ice-cold 50 mM Tris-HCl buffer (pH 7.7) using a polytron (setting for 6 to 20 seconds). The homogenate is centrifuged at 50,000×g for 10 minutes at 4° C. The pellet is again homogenized in a polytron in 20 vol of buffer, and centrifuged as before. The pellet is finally resuspended in 40 vol of 50 mM Tris-HCl (pH 7.7) per gram of original wet weight of tissue.

Incubation tubes, in triplicate, receive 100 $\mu$l of [3H]NECA (94 nM in the assay), 100 $\mu$l of 1 $\mu$M cyclohexyladenosine (CHA), 100 $\mu$l of 100 mM MgCl$_2$, 100 $\mu$l of 1 IU/ml adenosine deaminase, 100 $\mu$l of test compounds at various concentrations over the range of $10^{-10}$M to $10^{-4}$M diluted with assay buffer (50 mM Tris-HCl, pH 7.7) and 0.2 $\mu$l of membrane suspension (5 mg wet weight), in a final volume of 1 ml of 50 mM Tris-HCl, pH 7.7. Incubations are carried out at 25° C. for 60 minutes. Each tube is filtered through GF/B glass fiber filters using a vacuum. The filters are rinsed two times with 5 ml of the ice-cold buffer. The membranes on the filters are transferred to scintillation vials to which 8 ml of Omnifluor with 5% Protosol is added. The filters are counted by liquid scintillation spectrometry.

Specific binding of [3H]NECA is measured as the excess over blanks run in the presence of 100 $\mu$M 2-chloroadenosine. Total membrane-bound radioactivity is about 2.5% of that added to the test tubes. Since this condition limits total binding to less than 10% of the radioactivity, the concentration of free ligand does not change appreciably during the binding assay. Specific binding to membranes is about 50% of the total bound. Protein content of the membrane suspension is determined by the method of O. H. Lowry, N. J. Rosebrough, A. L. Farr and R. J. Randall, *Protein Measurements With Folin Phenol Reagent, J. Biol. Chem.*, 193, 265-275 (1951).

Displacement of [3H]NECA binding of 15% or more by a test compound is indicative of affinity for the adenosine A-2 site. The molar concentration of a compound which causes 50% inhibition of the binding of ligand is the $IC_{50}$. A value in the range of 100-1000 nM would indicate a highly potent compound.

Test For Affinity For Brain Adenosine A-1 Receptor Binding Sites

The test described below is used to determine the potency of test compounds to compete with the ligand [3H]cycloadenosine for the Adenosine A-1 receptor prepared from rat brain membranes. Male Sprague-Dawley rats are sacrificed by decapitation and the membranes are isolated from whole animal brains. (See R. Goodman, M. Cooper, M. Gavish, and S. Synder, *Guanine Nucleotide and Cation Regulation of the Binding of [H]Diethylphenylxanthine to Adenosine A-1 Receptors in Brain Membrane, Molecular Pharmacology*, 21, 329-335 (1982).

Membranes are homogenized (using polytron setting 7 for 10 seconds) in 25 volumes of ice-cold 50 mM Tris-HCl buffer, pH 7.7. The homogenate is centrifuged at 19,000 rpm for 10 minutes at 4° C. The pellet is washed by resuspending in 25 volumes of buffer with 2 IU of adenosine deaminase per ml and incubated 30 minutes at 37° C. The homogenate is centrifuged again. The final pellet is resuspended in 25 volumes of ice-cold buffer.

The incubation tubes, in triplicate, receive 100 $\mu$l of [3H]cyclohexyladenosine, 0.8 nM in the assay, 200 $\mu$l of test compounds at various concentrations over the range of $10^{-10}$M to $10^{-6}$M diluted with 50 nM Tris-HCl buffer (pH 7.7), 0.2 ml of membrane suspension (8 mg wet weight) and in a final volume of 2 ml with Tris buffer. Incubations are carried out at 25° C. for 2 hours and each one is terminated within 10 seconds by filtration through a GF/B glass fiber filter using a vacuum. The membranes on the filters are transferred to scintillation vials. The filters are counted by liquid scintillation spectrometry in 8 ml of Omniflour containing 5% Protosol.

Specific binding of [3H]cycloadenosine is measured as the excess over blanks taken in the presence of $10^{-5}$M 2-chloroadenosine. Total membrane-bound radioactivity is about 5% of that added to the test tubes. Specific binding to membranes is about 90% of the total bound. Protein content of the membrane suspension is determined by the method of Lowry, et al., Ibid, 265.

Displacement of [3H]cyclohexyladenosine binding of 15% or more by a test compound is indicative of affinity for the adenosine binding site.

Adenosine Receptor Binding Affinity Values Obtained Using The Above Described Test Procedures The following is a table showing the adenosine receptor binding affinities for several compounds (refer to compound examples on page 5 for cross reference to compound names) within the scope of the present invention:

| Compound | A-1 Receptor $K_i$ | A-2 Receptor $K_i$ | A-1 $K_i$/A-2 $K_i$ |
|---|---|---|---|
| 1. | $8.4 \times 10^{-6}$ | $3.5 \times 10^{-9}$ | 2400 |
| 2. | $5.8 \times 10^{-6}$ | $158 \times 10^{-9}$ | 37 |

The nucleotide guanosine triphosphate (GTP) has been shown to differentially affect the binding of agonists and antagonists to a variety of neurotransmitter receptors. In general, guanine nucleotides lower the affinity of agonists for receptors without a concomitant decrease in antagonist affinity. Accordingly, GTP has been shown to decrease the potency of agonists but not antagonists as inhibitors of the binding of the adenosine antagonist [3H]3-diethyl-8-phenylxanthine. In general, GTP greatly reduces the potency of purine agonists, but not antagonists as inhibitors of [3H]phenylisopropyl adenosine binding and is, therefore, an effective agent for distinguishing between agonists and antagonists. (See L. P. Davies, S. C. Chow, J. H. Skerritt, D. J. Brown and G. A. R. Johnston, Pyrazolo [3,4-d]Pyrimidines as Adenosine Antagonists, Life Sciences, 34, 2117–28 (1984). It is understood, in general, that adenosine analogs act as agonists if β-D-ribofuranosyl is present in the molecule at the $R_1$ position and as an antagonist if $R_1$ is hydrogen or phenyl.

Pharmaceutical Preparations of the Adenosine Receptor Selection Adenosine Analogs The exact amount of the compound or compounds to be employed, i.e., the amount of the subject compound or compounds sufficient to provide the desired effect, depends on various factors such as the compound employed; type of administration; the size, age and species of animal; the route, time and frequency of administration; and, the physiological effect desired. In particular cases, the amount to be administered can be ascertained by conventional range finding techniques.

The compounds are preferably administered in the form of a composition comprising the compound in admixture with a pharmaceutically acceptable carrier, i.e., a carrier which is chemically inert to the active compound and which has no detrimental side effects or toxicity under the conditions of use. Such compositions can contain from about 0.1 μg or less to 500 mg of the active compound per ml of carrier to about 99% by weight of the active compound in combination with a pharmaceutically-acceptable carrier.

The compositions can be in solid forms, such as tablets, capsules, granulations, feed mixes, feed supplements and concentrates, powders, granules or the like; as well as liquid forms such as sterile injectable suspensions, orally administered suspensions or solutions. The pharmaceutically acceptable carriers can include excipients such as surface active dispersing agents, suspending agents, tableting binders, lubricants, flavors and colorants. Suitable excipients are disclosed, for example, in texts such as Remington's Pharmaceutical Manufacturing, 13 Ed., Mack Publishing Co., Easton, Pa. (1965).

The following examples present typical syntheses as described by Scheme A. These examples are understood to be illustrative only and are not intended to limit the scope of the invention in any way. As used in the following examples, the following terms have the meanings indicated: "$[\alpha]_D^{20}$" refers to the optical rotation of the compound at 20° C. using a sodium D light, "g" refers to grams, "mmol" refers to millimoles, "ml" refers to milliliters, "° C." refers to degrees Celsius, "TLC" refers to thin layer chromatography, "mg" refers to milligrams, "μl" refers to microliters, and "δ" refers to parts per million downfield from tetramethylsilane.

EXAMPLE 1

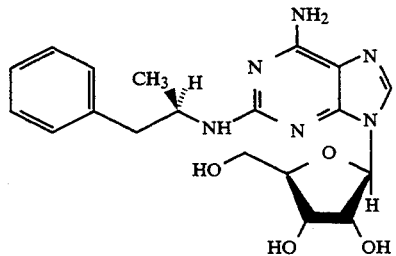

(R)-2-[(Phenylisopropyl)Amino]Adenosine

Scheme A, Step A

Combine 2-chloroadenosine hemihydrate (0.96 g, 3.09 mmol), 2,2-dimethoxypropane (3.2 g, 30.9 mmol) and p-toluenesulfonic acid (2.93 g, 15.5 mmol) in N,N-dimethlyformamide (40 ml). Stir the reaction for 20 hours and then add saturated sodium bicarbonate (70 ml). Concentrate the reaction under vacuum. Extract the residue with chloroform (3×300 ml). Combine the organic extracts, dry over anhydrous magnesium sulfate, filter, and concentrate under vacuum. Purify the residue by radial chromatography (5% methanol/chloroform, 4 mm plate) to provide 1.14 g of the acetonide (2).

Scheme A, Step B

Combine the acetonide (2) (444 mg, 0.13 mmol) with L-(—)-amphetamine (3.4 g) and heat to 130° C. for 3.5 hours under nitrogen with stirring. After cooling, purify by flash chromatography (3% to 4% to 5% methanol/chloroform) followed by radial chromatography (3% to 4% to 5% methanol/chloroform, 4 mm plate) to provide the secondary amine (3) (262 mg).

Scheme A, Step C

Treat the secondary amine (3) (249 mg, 0.57 mmol) with 1M hydrochloric acid (20 ml) and heat the reaction to 50° C. for 30 minutes. Cool the reaction and pour into saturated sodium bicarbonate (200 ml). Extract the reaction with chloroform (3×150 ml). Combine the organic extracts, dry over anhydrous magnesium sulfate, filter, and concentrate under vacuum. Purify the residue by radial chromatography (2% to 4% to 8% to 15% methanol/chloroform, 4 mm plate) four times to provide the title compound (105 mg) as the free base. Treat this with ethereal hydrogen chloride, filter, and dry the solid under high vacuum over phosphorous pentoxide to provide the hydrochloride salt of the Formula I (48 mg), m.p. 153° C. dec.; $[\alpha]_D^{20} = 30°$ (c=1.04, H$_2$O)

EXAMPLE 2

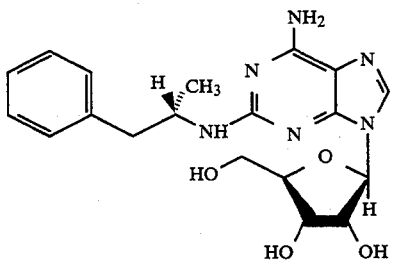

(S)-2-[(Phenylisopropyl)Amino]Adenosine

Scheme A, Step A

Combine 2-chloroadenosine hemihydrate (0.96 g, 3.09 mmol), 2,2-dimethoxypropane (3.2 g, 30.9 mmol), and p-toluenesulfonic acid (2.93 g, 15.5 mmol) in N,N-dimethlyformamide (40 ml). Stir the reaction for 20 hours and then add saturated sodium bicarbonate (70 ml). Concentrate the reaction under vacuum. Extract the residue with chloroform (3×300 ml). Combine the organic extracts, dry over anhydrous magnesium sulfate, filter, and concentrate under vacuum. Purify the residue by radial chromatography (5% methanol/chloroform, 4 mm plate) to provide 1.14 g of the acetonide (2).

Scheme A, Step B

Combine the acetonide (2) (638 mg, 1.87 mmol) with D-(+)-amphetamine (4.5 g) and heat to 130° C. for 5 hours under nitrogen with stirring. After cooling, purify by flash chromatography (3% to 5% to 10% methanol/chloroform) followed by radial chromatography four times (2% to 4% to 6% to 8% to 10% methanol/chloroform, 4 mm plate) to provide the secondary amine (3) (0.56 g).

Scheme A, Step C

Treat the secondary amine (3) (0.46 g, 1.05 mmol) with 1M hydrochloric acid (40 ml) and heat the reaction to 45° C. for 15 minutes. Cool the reaction and pour into saturated sodium bicarbonate (300 ml). Extract the reaction with chloroform (3×150 ml). Combine the organic extracts, dry over anhydrous magnesium sulfate, filter, and concentrate under vacuum to provide the title compound (0.40 g) as the free base. Treat this with ethereal hydrogen chloride, filter, and dry the solid under high vacuum over phosphorous pentoxide. Recrystallize from 10% methanol/diethyl ether to provide, after drying under high vacuum over phosphorous pentoxide, the hydrochloride salt of the Formula I (184 mg), m.p. 155° C. dec.; $[\alpha]_D^{20} = +9.75°$ (c=1.01, H$_2$O).

EXAMPLE 3

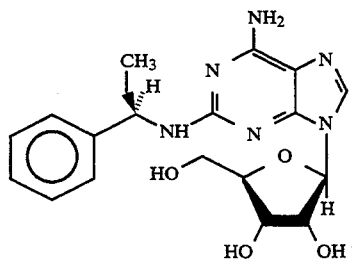

(R)-2-(1-Phenylpropyl)Amino]Adenosine

Scheme A, Step B

Combine the acetonide (2) (3.4 g, 9.95 mmol) with (R)-1-phenylpropylamine (8.62 g) and heat to reflux for 18 hours. Remove some of the excess amine by distillation. After cooling, purify by flash chromatography (3% methanol in dichloromethane). Triturate the product with diethyl ether to provide the secondary amine (3) (1.38 g); $^1$H NMR (CDCl$_3$) δ 7.41 (1H, s), 7.21–7.34 (4H, m), 7.14–7.22 (1H, m), 5.69 (1H, d), 5.50 (2H, s), 5.25 (1H, d), 5.10 (1H, t), 5.01 (1H, q), 4.90 (1H, q), 4.41 (1H, s), 3.93 (1H, d), 3.80 (1H, d), 1.82 (2H, pent), 1.60 (3H, s), 1.32 (3H, s), 0.94 (3H, t); IR (KBr) 3450-3100, 1633, 1599 cm$^{-1}$. Anal. Calcd for C$_{22}$H$_{28}$N$_6$O$_4$: C, 59.99; H, 6.41; N, 19.08. Found: C, 59.99; H, 6.38; N, 18.71.

Scheme A, Step C

Dissolve the above secondary amine (3) with trifluoroacetic acid (20 ml) and treat with water (2 ml). After 15 minutes remove the solvent under vacuum. Treat the residue with water/dichloromethane and make the aqueous basic with saturated sodium bicarbonate. Separate the layers, dry the organic phase over anhydrous sodium sulfate, filter, and concentrate under vacuum. Purify the resulting solid by flash chromatography (5% to 10% to 15% methanol/dichloromethane) and then recrystallize from acetone to provide the title compound (62 mg); $^1$H NMR (DMSO-d$_6$) δ 7.87 (1H, s), 7.38 (1H, d), 7.27 (2H, t), 7.16 (1H, t), 6.60–6.73 (3H, m, exchangeable), 5.69 (1H, d), 5.31 (1H, d), 5.02+5.12 (2H, brs+d), 4.83 (1H, q), 4.52 (1H, dd), 4.17 (1H, dd), 3.88 (1H, dd), 3.64–3.73 (1H, m), 3.47–3.59 (1H, m), 2.08 (3H, s, Me$_2$SO), 1.63–1.89 (2H, m), 0.96 (3H, t); IR (KBr) 3423-3290 cm$^{-1}$. Anal. Calcd for C$_{19}$H$_{24}$N$_6$O$_4$·½C$_3$H$_6$O: C, 57.33; H, 6.34; N, 19.57. Found: C, 59.96; H, 6.73; N, 19.92.

What is claimed is:

1. The compound (R)-2-[(phenylisopropyl)amino]adenosine whose structure is given below:

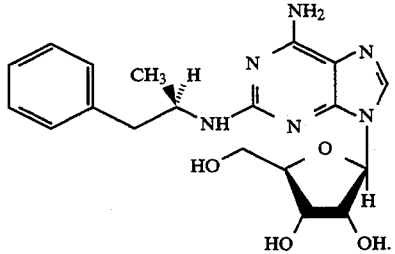

2. A method of treating hypertension in a patient in need thereof which comprises administering to the patient a therapeutically effective amount of a compound according to claim 1.

3. A compound which is (R)-2-[(phenylisopropyl)-]amino]adenosine hydrochloride.

4. A method of treating hypertension in a patient in need thereof which comprises administering to the patient a therapeutically effective amount of a compound according to claim 3.

* * * * *

UNITED STATES PATENT AND TRADEMARK OFFICE
CERTIFICATE OF CORRECTION

PATENT NO. : 5,426,101

DATED : June 20, 1995

INVENTOR(S) : Norton P. Peet, et al.

It is certified that error appears in the above-identified patent and that said Letters Patent is hereby corrected as shown below:

At Column 3, line 13, the patent reads "[iJ." and should read --[J--.
At Column 7, line 7, the patent reads "recieved" and should read --received--.
At Column 7, line 22, the patent reads "less that" and should read --less than--.
At Column 8, line 45, the patent reads "Synder" and should read --Snyder--.
At Column 8, line 47, the patent reads "[H]" and should read --[3H]--.
At Column 11, line 29, the patent reads "Step A" and should read --Step a--.
At Column 11, line 43, the patent reads "Step B" and should read --Step b--.
At Column 11, line 52, the patent reads "Step C" and should read --Step c--.
At Column 12, line 15, the patent reads "Step B" and should read --Step b--.
At Column 12, line 29, the patent reads "Step C" and should read --Step c--.

Signed and Sealed this

Twenty-third Day of April, 1996

Attest:

BRUCE LEHMAN

*Attesting Officer*     *Commissioner of Patents and Trademarks*